United States Patent [19]

Helmlinger et al.

[11] Patent Number: 4,617,146

[45] Date of Patent: Oct. 14, 1986

[54] SUBSTITUTED BICYCLO[4.3.0]NON-1(6)-EN-8-YL METHYL KETONES AND FRAGRANCE AND FLAVOR COMPOSITIONS

[75] Inventors: Daniel Helmlinger, Gockhausen; Mario Pesaro, Zurich, both of Switzerland; Michael Klaus, Weil am Rhein, Fed. Rep. of Germany

[73] Assignee: Givaudan Corporation, Clifton, N.J.

[21] Appl. No.: 569,019

[22] Filed: Jan. 9, 1984

[30] Foreign Application Priority Data

Jan. 13, 1983 [CH] Switzerland ............................ 189/83

[51] Int. Cl.⁴ ........................ A61K 7/46; A23L 2/26; C07C 49/105
[52] U.S. Cl. .............................. 252/522 R; 426/538; 568/374
[58] Field of Search .................... 252/522 R; 426/538; 568/374

[56] References Cited

U.S. PATENT DOCUMENTS

| | | | |
|---|---|---|---|
| 2,933,506 | 4/1960 | Ohloff | 568/374 X |
| 3,847,993 | 11/1974 | Hall et al. | 568/374 X |
| 3,929,677 | 12/1975 | Hall et al. | 568/374 X |
| 4,076,749 | 2/1978 | Schreiber et al. | 568/374 X |
| 4,156,695 | 5/1979 | Schreiber et al. | 568/374 X |

FOREIGN PATENT DOCUMENTS

| | | | |
|---|---|---|---|
| 0021356 | 1/1981 | European Pat. Off. | 252/522 R |
| 2622611 | 1/1977 | Fed. Rep. of Germany | 252/522 R |
| 3023483 | 1/1982 | Fed. Rep. of Germany | 252/522 R |

OTHER PUBLICATIONS

E. T. Theimer, "Fragrance Chemistry, The Science of the Sense of Smell", 1982, Academic Press, New York, NY Chap 14, pp. 514–524.

Primary Examiner—Anton H. Sutto
Attorney, Agent, or Firm—Robert F. Tavares

[57] ABSTRACT

This invention is concerned with novel substituted bicyclo[4.3.0]non-1(6)-yl methyl ketones, a process for their manufacture and novel fragrance and flavor compositions containing same.

9 Claims, No Drawings

SUBSTITUTED BICYCLO[4.3.0]NON-1(6)-EN-8-YL METHYL KETONES AND FRAGRANCE AND FLAVOR COMPOSITIONS

THE INVENTION

This invention is concerned with novel compounds of the formula

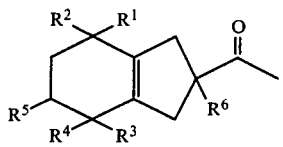   I wherein:
$R^1$, $R^2$, $R^3$ and $R^4$ represent hydrogen, methyl, ethyl or isopropyl provided that $R^1$, $R^2$, $R^3$ and $R^4$ are not alike unless they represent methyl, and,
$R^5$ and $R^6$ represent hydrogen or methyl.

The compounds of formula I possess organoleptic properties which make them particularly useful as odorants and flavorants.

The invention is also concerned with a process for the manufacture of the compounds of formula I and with fragrance and flavor compositions containing the same.

DESCRIPTION OF THE PREFERRED EMBODIMENTS

The compound of formula I can be prepared by:
(a) oxidatively rearranging a compound of the formula

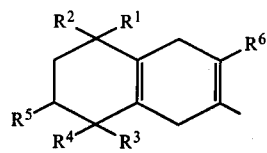   II wherein
$R^1$ to $R^5$ have the above significance
and $R^6$ represents hydrogen, under ring contraction, or
(b) isomerizing a compound of the formula

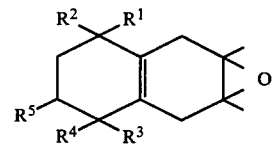   IV wherein
$R^1$ to $R^5$ have the above significance, or
(c) rearranging a compound of the formula

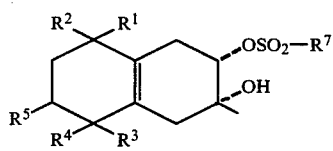   VI wherein
$R^1$ and $R^5$ have the above significance
and $R^7$ represents a lower alkyl or aryl group, under ring contraction.

The following Reaction Scheme in which $R^1$ to $R^7$ have the above significance illustrates these three process variants and also the preparation of the starting materials for formulas II, IV and VI.

Reaction Scheme I

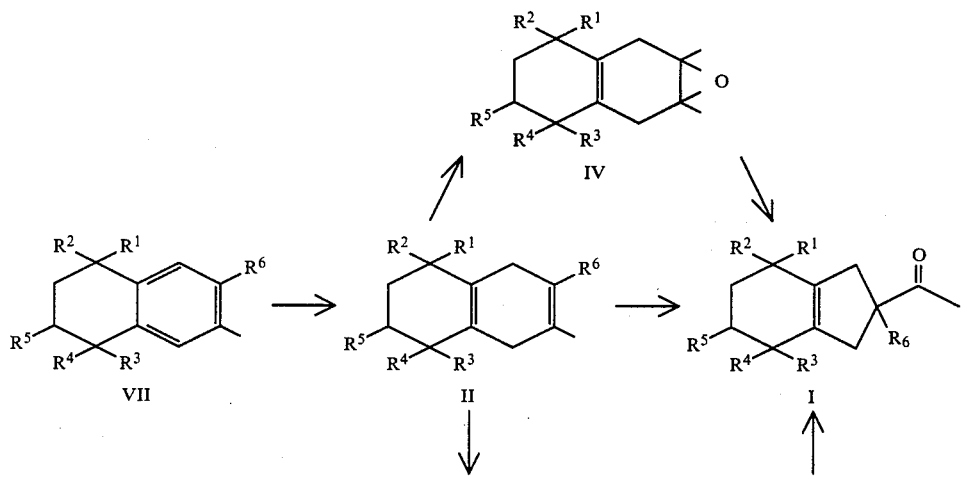

-continued
Reaction Scheme I

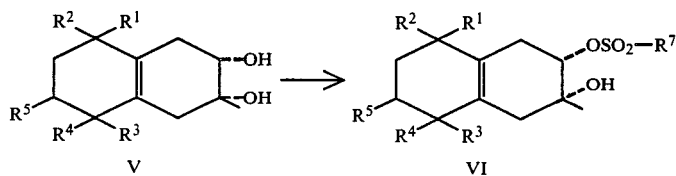

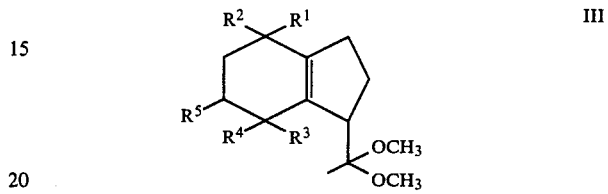

The substituted 6-methyltetralin of formula VII can be reduced to the bicyclic 1,4-diene of formula II by known reduction methods such as those of Birch [see, for example, A. J. Birch, G. Subba Rao, Advances in Organic Chemistry 8, 1 (1972)] Benkeser [see, for example, R. Benkeser, J. Org. Chem. 24, 854 (1959) and 29, 955, 1313 (1964)]. The reduction may be carried out with an alkali metal or alkaline earth metal such as, for example, lithium, sodium or calcium and an alcohol in liquid ammonia or an alkylamine. A solvent such as diethyl ether, tetrahydrofuran or dimethoxyethane may be used if desired. The temperature of the reaction may range from −40° C. to the boiling point of the amine. It is preferred to conduct the reaction at a temperature 5°–6° C. below the boiling point of the amine.

In addition to the diene of formula II this reduction method also results in the formation of the byproduct tetrahydo compounds of formula II'

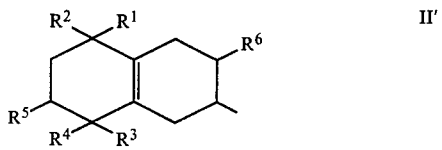

wherein $R^1$ to $R^5$ have the same significance as above. While the compounds of formula II' are separable from the compounds of formula II by means such as gas chromatography it is not necessary to do so since the presence of these compounds does not adversely affect succeeding reactions, and it is therefore more economical to use such mixtures as the starting materials in the process.

When $R^6$ of formula II represents hydrogen the compounds of formula I may be prepared by process variant (a) described previously. This process comprises an oxidative rearrangement of an olefin, involves a ring contraction and uses thallium (III) nitrate as the reagent [see A. Mc Killop, Pure Appl. Chem. 43, 463(1975)]. This reaction takes place under mild conditions at room temperature in an alcoholic solvent, preferably, methanol. After filtering off the thallium (I) salt, neutralizing the nitric acid by pouring the filtrate onto sodium bicarbonate, and removing the solvent the product can be purified by ordinary distillation methods such as fractional high vacuum distillation. Some dimethyl ketal of the formula wherein $R^1$ and $R^5$ have the above significance, is also formed as a by-product. These compounds of formula III need not be separated from the compounds of formula I since their presence does not have a detrimental effect on the organoleptic properties of the compounds of formula I. If desired, however, the compounds can be separated, (e.g., by Chromatography).

When $R^6$ of formula II represents methyl the preferred synthesis of the compounds of formula I follows process variant (b) described above and outlined in Reaction Scheme I. This synthesis requires compounds of formula IV. The 1,4-dienes of formula II are preferably converted into the bicyclic epoxides of formula IV by known epoxidation methods. Especially preferred methods are those using peracids such as, for example, peracetic acid, and metachloroperbenzoic acid. The isomerization of the bicyclic epoxides of formula IV to the novel compounds of formula I in which $R^6$ represents methyl (process variant b) is preferably carried out in the presence of an acidic catalyst, especially a Lewis acid catalyst such as boron trifluoride etherate. The exothermic reaction is preferably carried out with external cooling which allows the temperature in the reaction mixture to be held at a maximum of 50° C. The reaction time is about 30 minutes.

Compounds of formula II in which $R^6$ represents hydrogen may be oxidized to the cis-1,2-diols of formula V by known oxidizing agents such as trimethylamine N-oxide, N-methylmorpholine oxide, hydrogen superoxide, tertiary butyl hydroperoxide/tetramethylammonium acetate, chlorates or potassium permanganate. Osmium tetroxide may be used as the catalyst or when used in stoichiometric amounts, as the oxidizing agent. Solvents such as tert-butanol or acetone are preferred. When osmium tetroxide is used as the oxidizing agent, then pyridine is the preferred solvent. Th oxidation may be carried out in a two-phase system using phase transfer catalysts such as, for example, benzyltrimethylammonium chloride [see, for example, R. Criegée, M. Kropf, Methoden der organischen Chemie (Houben-Weyl), Vol. VI, Part 1a, p. 592, Georg Thieme Verlag Stuttgart 1979]. The cis-1,2-diol of formula V is subsequently converted into the monosulfonate of formula VI in which $R^7$ represents lower alkyl or aryl. This conversion is carried out according to known methods, for example, using the corresponding sulfochloride of the formula $R^7$—$SO_2$—Cl in pyridine. The ring contraction required in the conversion of the compounds of formula VI into the compounds of formula I (process variant c) is conveniently carried out by the addition of a strong inorganic base such as, sodium hydroxide or potassium hydroxide in aqueous-alcoholic solutions. The reaction can be run at mild reaction temperatures, preferably at room temperature and is usually complete in less than 24 hours.

Depending on the nature and number of the substitutions $R^1$ to $R^6$, the compounds of formula I can be obtained as mixtures of diastereomers or mixtures of structural isomers. The mixtures can be separated into the individual components by separation techniques such as gas chromatography. It is more economical, however, not to effect a separation and to use the mixtures as such.

As mentioned earlier, a separation of the by-products of formula II' from the compounds of formula II and of the by-products of formula III from the compounds of formula I is not necessary. The presence of the by-products has no detrimental influence on the sensorial qualities of the novel compounds of formula I.

The compounds of formula I have particular organoleptic properties, on the basis of which they are excellently suited as odorant and flavoring substances. They are distinguished, in particular, by a combination of fruity, damascone-like musk notes which hitherto were missing in the pallette of the perfumer. In addition, some of these compounds have an odour in the direction of ambrette-seeds or exhibit berry-like notes of the ionone direction.

On the basis of their natural odour notes the compounds of formula I are suitable, in particular, for modifying known compositions, for example (a) flowery compositions in which, for example, the warm notes are to be intensified, (e.g., for mens cologne), (b) fruity compositions such as those of the raspberry type (essence types, compositions of the feminine direction), (c) tobacco and woody compositions (essence types of the masculine direction) and (d) compositions with green notes, wherein a desired rounding-off and harmonizing effect are produced.

Preferred compounds are 2,2,5,5-tetramethylbicyclo[4.3.0]non-1(6)-en-8-yl methyl ketone and 2,2,3,5,5-pentamethylbicyclo[4.3.0]non-1(6)-en-8-yl methyl ketone.

The first-named preferred compound may be synthesized by a route outlined in Reaction Scheme II.

Reaction Scheme II

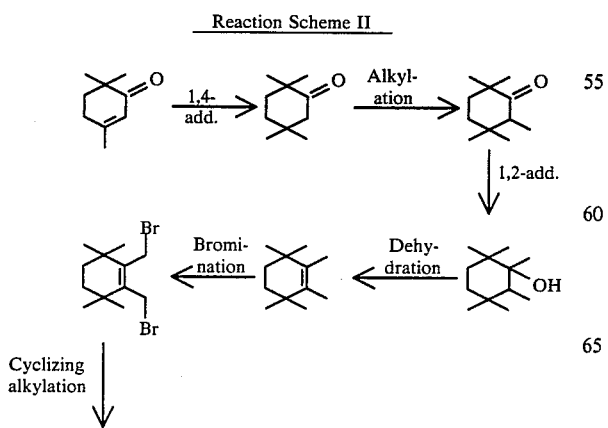

-continued
Reaction Scheme II

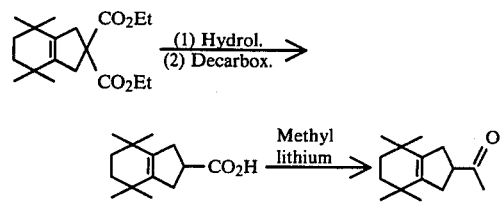

Methyl lithium is added to 3,6,6-trimethylcyclohex-2-en-1-one in the presence of a cuprous salt. The resulting saturated tetramethyl-substituted cyclohexanone is subsequently methylated in the 2-position with methyl iodide and the ketone obtained is converted by known methods (1,2-addition) into the tertiary alcohol 1,2,3,3,6,6-hexamethylcyclohexanol. This alcohol is dehydrated in the presence of a mineral acid or a strong organic sulfonic acid, and the resulting hexamethylcyclohexanene is brominated with monobromination occuring on each of the vinylic methyl groups. The resultant dibromide is used as the alkylating agent for the cyclic alkylation of diethyl malonate. The reaction product which results is saponified and decarboxylated according to known methods yieldling 2,2,5,5-tetramethylbicyclo [4.3.0]-non-1(6)-ene-8-carboxylic acid. In the last step, methyl lithium is used to convert the carboxylic acid to the corresponding novel methyl ketone.

As odorant substances, the compounds of formula I on the basis of their original notes described above are suitable, in particular, in combination with a series of natural and synthetic odorant substances such as, for example:

Natural products
such an angelica root oil, galbanum oil, vetiver oil, patchouli oil, sandalwood oil, mandarin oil, ylang ylang oil, cedar oil, pine oil, lavender oil, bergamot oil, lemon oil, orange oil, coriander oil, oak moss, castoreum, ciste labdanum, calamus oil, geranium oil, jasmine absolute, rose oil, cassis absolute, narcissus absolute, vervain absolute etc.

Aldehydes
such as $C_{10}$-, $C_{11}$-, $C_{14}$-, $C_{16}$-, $C_{18}$-aldehyde, hydroxycitronellal, cyclamen aldehyde, benzaldehyde, p.-tert.-butyl-$\alpha$-methylcinnamaldehyde, citral, citronellal, 2,6-dimethyl-5-hepten-1-al, isovaleraldehyde, trans-2-hexenal, sorbic aldehyde, trans-2-octenal, n-octanal, n-nonanal, trans-2-cis-6-nonadienal, 2,4-decadienal, methylnonyl-acetaldehyde etc.

Ketones
such as alpha-ionone, beta-ionone, methylionone, allylionone, acetanisole, 4-(para-hydroxyphenyl)-2-butanone, camphor, menthone, carvone, pulegone etc.

Acetals and ketals
such as phenylacetaldehyde dimethyl acetal, phenylacetaldehyde glycerine acetal, 2-methyl-1,3-dioxolan-2-ethyl acetate, caproaldehyde dimethyl acetal etc.

Ethers
such as eugenol methyl ether, methyl 1-methylcyclododecyl ether, anethol, estragol etc.

Phenol compounds
such as vanillin, eugenol, isoeugenol, creosol etc.

Alcohols such as butanol, n-hexanol, cis-3-hexenol, trans-2,cis-6-nonadienol, cis-6-nonenol, linalool, geraniol, nerol, citronellol, nerolidol, farnesol, benzyl alcohol, phenylethyl alcohol, cinnamic alcohol etc.

Esters such as ethyl formate, ethyl acetate, isoamyl acetate, t-butylcyclohexyl acetate, Myraldylacetat TM (Givaudan), benzyl acetate, styrallyl acetate, ethyl-α-methylphenyl-glycidate, maltyl isobutyrate, dimethylbenzylcarbinyl butyrate, linalyl acetate, isobutyl acetate, n-amyl butyrate, n-amyl valerate, ethyl palmitate, cinnamyl formate, terpenyl acetate, geranyl acetate, hexyl salicylate, linalyl anthranilate, amyl salicylate, methyl dihydrojasmonate.

Lactones such as γ-undecalactone, γ-decalactone, γ-nonalactone, δ-decalactone, δ-octalactone, coumarin etc.

Acids such as lactic acid, butyric acid, α-methylbutyric acid, trans-2-hexenoic acid, trans-2-octenoic acid etc.

Sulphur-containing compounds such as p-menthane-8-thiol-3-one, dimethyl sulphide and other sulphides and disulphides etc.

Nitrogen-containing compounds such as methyl anthranilate, indole, isobutylquinoline, various pyrazines, 5-methyl-heptan-3-one oxime etc.

Various additional components often used in perfumery such as musk ketone, Musk 174 TM (12-oxahexadecanolide), Sandela (3-isocamphyl-(5)-cyclohexanol).

The compounds of formula I can be used in wide limits which, for example, can extend in compositions from 0.1% (detergents) to 50% (alcoholic solutions). It will be appreciated that these values are not limiting values, since the experienced perfumer can also produce effects with even lower concentrations or can synthesize novel complexes with even higher concentrations. The preferred concentrations range between 0.5% and 20%. The compositions manufactured with the compounds of formula I can be used for all kinds of perfumed consumer goods (eau de cologne, eau de toilette, essences, lotions, creams, shampoos, soaps, salves, powders, deodorants, detergents, tobacco etc).

The compounds of formula I can accordingly be used in the manufacture of compositions and, as will be evident from the above compilation, a wide range of known odorant substances can be used. In the manufacture of such compositions the known odorant substances specified above can be used according to methods which are known to the perfumer such as, for example, according to W. A. Poucher, Perfumes, Cosmetics and Soaps 2, 7th Edition, Chapman and Hall, London, 1974.

The compounds of formula I are also excellently suited for use in fruit flavours of various kinds, but especially also for the flavouring of tobacco.

As flavouring substances the compounds of formula I can be used, for example, for the production or improvement, intensification, enhancement or modification of fruit flavours of various kinds (e.g. blackberry or apricot flavours). As fields of use for these flavours there come into consideration, for example, foodstuffs (yoghurt, confectionery etc), semi-luxury consumables (tea, tobacco etc) and drinks (lemonade etc).

The pronounced flavour properties of the compounds of formula I enable them to be used in low concentrations. A suitable concentration embraces, for example, the range of 0.01–100 ppm, preferably 0.1–20 ppm, in the finished product, i.e. the flavoured foodstuffs, semi-luxury consumable or drink.

In the flavouring of, for example, tobacco, the concentration can, however, also be higher and can embrace a wider range, for example the range of 1 to 1000 ppm, preferably 50–500 ppm.

The compounds can be mixed with the ingredients used for flavouring substance compositions or added to such flavourants in the usual manner. Under the flavourants used in accordance with the invention there are to be understood flavouring substance compositions which can be diluted or dispersed in edible materials in a manner known per se. They contain, for example, about 0.1–10 wt.%, especially 0.5–3 wt.%. They can be converted according to methods known per se into the usual forms of use such as solutions, pastes or powders. The products can be spray-dried, vacuum-dried or lyophilized.

The known flavouring substances conveniently used in the manufacture of such flavourants are either mentioned in the above compilation or can be concluded readily from the literature such as, for example, from J. Merory, Food Flavourings, Composition, Manufacture and Use, Second Edition, The Avi Publishing Company Inc., Westport, Conn. 1968, or G. Fenaroli, Fenaroli's Handbook of Flavour Ingredients, Second Edition, Volume 2, CRC Press, Inc. Cleveland, Ohio, 1975.

For the manufacture of such usual forms of use there come into consideration, for example, the following carrier materials, thickening agents, flavour improvers, spices and auxiliary ingredients etc:

Gum arabic, tragacanth, salts or brewers' yeast, alginates, carrageen or similar absorbents; indoles, maltol, dienals, spice oleoresins, smoke flavours; cloves, diacetyl, sodium citrate; monosodium glutamate, disodium inosine-5'-monophosphate (IMP), disodium guanosine-5-phosphate (GMP); or special flavouring substances, water, ethanol, propylene glycol, glycerine.

EXAMPLES

The following Examples illustrate the present invention:

EXAMPLE 1

160 ml of methylamine are placed in a three-necked sulphonation flask equipped with a stirrer and a low temperature condenser (filled with $CO_2$/isopropanol) and 40 g (0.2M) of 1,1,4,4,6-pentamethyl-1,2,3,4-tetrahydro-naphthalene and 18 g (0.4M) of ethanol are added. The mixture is cooled to −15° C. and 2.7 g of lithium in small pieces are added. After 10 minutes, there are added a further 9 g (0.2M) of ethanol and subsequently a further 1.4 g (0.2M) of lithium in small pieces. The entire lithium dissolves within 15 minutes. The methylamine is then distilled off and the residue is diluted with hexane. The organic phase is washed neutral with water, dried over sodium sulphate and evaporated. 40 g of crude product are obtained. This product contains (according to GC):

55%: 2,2,5,5,8-Pentamethyl-bicyclo[4.4.0]deca-1(6),8-diene. $^1$H-NMR ($CDCl_3$ 400 MHz): 0.99 (s, 3H); 1.01 (s, 3H); 1.5 (s, 4H); 1.68 (m, 3H); 2.54 (m, 2H); 2.65 (m, 2H); 5.42 (m, 1H); MS: M+ 204, 189, 175, 161, 133, 119, 105, 93, 81.

7%: 2,2,5,5,8-Pentamethyl-bicyclo[4.4.0]deca-1(10),7,-diene, $^1$H-NMR (CDCl$_3$ 400 MHz); 0.63 (s, 3H); 0.99 (s, 3H); 1.03 (s, 3H); 1.07 (s, 3H); 1.69 (s, 3H); 5.43 (m, 1H); 5.50 (m, 1H); MS: 204, 189, 145, 135, 133, 119, 105, 91, 77, 69, 55, 41, 27.

30%: 2,2,5,5,8-Pentamethyl-bicyclo[4,4,0]deca-1(6)-ene.

6%: Starting material.

253.3 g of hydrocarbon mixture containing about 60% of 2,2,5,5,8-pentamethyl-bicyclo[4.4.0]deca-1(6),8-diene are dissolved in 1050 ml of tert.butanol and treated with a solution of 91.65 g of trimethylamine N-oxide dihydrate in 375 ml of water. Thereto there is added a solution of 40 mg of osmium tetroxide in 75 ml of tert.butanol and the mixture is held for 48 hours at 95° C. with good stirring at reflux temperature. The solution is extracted with 2 l of dichloromethane, 1 l of water and 412.5 ml of 2N hydrochloric acid and ice. The organic phase is washed neutral twice with 1 l of water each time and the aqueous phases are extracted with dichloromethane. After drying over magnesium sulphate and concentration on a rotary evaporator, there are obtained 269 g of crude crystals. These are recrystallized from 150 ml of hexane and 80 ml of dichloromethane. There are obtained 167.0 g of crystalline 2,2,5,5,8-pentamethyl-bicyclo[4.4.0]dec-1(6)-ene-8,9-diol of melting point 98°–99.5° C.

$^1$H-NMR: (400 MHz, CDCl$_3$): δ (ppm) 0.96 (s, 3H); 0.97 (s, 3H); 0.98 (s, 3H); 1.00 (s, 3H); 1.19 (s, 3H); 1.48 (s, 4H); 3.58 (m, 1H).

MS ($^m$/e): 238 (M+), 220, 205, 177, 161, 149, 135, 121, 109, 105

150 g of the diol are dissolved completely at room temperature in 406.8 ml of pyridine while stirring. To this solution (cooled to 0° C.) are added dropwise during 30 minutes 82.9 g of methanesulphonyl chloride and the mixture is stirred at 20° C. for 3.5 hours. The suspension is poured into 1 l of dichloromethane and washed with 2.77 l of 2N hydrochloric acid and with sodium chloride solution. The aqueous phases are extracted twice with 500 ml of dichloromethane each time. The combined organic phases are dried over magnesium sulphate and concentrated on a rotary evaporator. After drying in a high vacuum at room temperature, there are obtained 198.5 g of crystalline monomesylate of the diol which, after recrystallization from dichloromethane/hexane, melts at 100°–104° C. with decomposition.

198.5 g of the crude monomesylate are dissolved completely at room temperature in 1190 ml of methanol and treated with 1190 ml of 3N potassium hydroxide solution. The mixture is stirred at 20° C. for 26 hours, taken up in hexane and washed with water. The aqueous phases are extracted twice with hexane. The combined organic phases are dried over magnesium sulphate and concentrated on a rotary evaporator. There are obtained 134.3 g of oil which is distilled over a 15 cm Widmer column. The fraction of boiling point 70°–76° C./0.03 Torr and n$_D^{20}$ 1.4868 (106.4 g) represents pure 2,2,5,5-tetramethyl-bicyclo[4.3.0]non-1(6)-en-8-yl methyl ketone.

EXAMPLE 2

200 g of hydrocarbon mixture containing 60% of 2,2,5,5,8-pentamethyl-bicyclo[4.4.0]deca-1(6),8-diene are dissolved in 2 l of methanol and 280 g (0.71M) of thallium (III) nitrate are added while stirring. A sample is removed (GC) after stirring for 48 minutes at room temperature. The reaction has still not finished. A further 50 g (0.12M) of thallium (III) nitrate are added after stirring for 57 minutes. After stirring for 2 hours the thallium (I) nitrate (184 g, 0.69M) is filtered off. The solution is poured cautiously while stirring on to 160 g of sodium bicarbonate. The mixture is stirred at room temperature for 30 minutes. The methanol is distilled off on a rotary evaporator in the presence of a small amount of sodium bicarbonate. The residue is washed with a small amount of ether. The crude product (208 g) is distilled in a high vacuum. After two-fold distillation (Widmer column, packed column 60 cm), there are obtained 56 g of product.

Separation by gas chromatography and analysis:

72%: 2,2,5,5-Tetramethyl-bicyclo[4.3.0]non-1(6)-en-8-yl methyl ketone. $^1$H-NMR (CDCl$_3$ 400 MHz): 0.96 (s, 3H); 0.975 (s, 3H); 1.44 (s, 3H); 2.15 (s, 3H); 2.52 (d, J=8 Hz, 4H); 3.09 (m, J=8 Hz, H$_3$, 1H); IR: 1710 cm$^{-1}$; MS: 220 M$^{30}$, 205, 177, 161, 145, 133, 119, 105, 91, 79, 55, 43. Odour: ambrette-musk, fruity, damascone.

9%: 1-(2,2,5,5-Tetramethyl-bicyclo[4.3.0]non-1(6)-en-7-yl)-1,1-dimethoxyethane. $^1$H-NMR (CDCl$_3$ 400 MHz): 0.95 (s, 9H); 1 (s, 3H); 1.08 (s, 3H); 3.29 (s, 3H); 3.34 (q, J=8, J=6 Hz, 1H); 3.43 (s, 3H); MS: 266, 234, 219, 203, 187, 175, 163, 147, 133. 119, 102, 91, 59.

EXAMPLE 3

600 ml of methylamine are placed in a three-necked sulphonation flask equipped with a stirrer and a low temperature condenser (filled with CO$_2$/isopropanol). There are now added 100 g of 1,1,3,4,4,6-hexamethyl-1,2,3,4-tetrahydro-naphthalene and 42.6 g (0.92M) of ethanol. The mixture is then cooled to −15° C. and 6.5 g (0.93M) of lithium in small pieces are added within 75 minutes. As long as the lithium has not reacted completely the mixture is cooled to −15° C. and then it is held at reflux temperature overnight. After 19.5 hours and after 25.5 hours, there are added at −15° C. within 30 minutes 3.25 g (0.46M) of lithium. The methylamine is distilled off after 29 hours. The residue is diluted with hexane, washed four times with water, once with 5% sulphuric acid and once more (neutral) with water, dried over sodium sulphate and evaporated. 82 g of crude product are obtained. This product contains (according to GC):

47%: 2,2,4,5,5,8-Hexamethyl-bicyclo[4.4.0]deca-1(6),8-diene. $^1$H-NMR (CDCl$_3$ 360 MHz): 0.83 (s, 3H); 0.88 (d, J=7 Hz, 3H); 0.96 (s, 3H); 1 (s, 3H); 1.02 (s, 3H): 1.68 (s, 3H); 5.41 (m, 1H); MS: 218, 203, 175, 159, 147, 133, 119, 105, 91 83.

29% 2,2,4,5,5,8-Hexamethyl-bicyclo[4.4.0]dec-1(6)-ene.

154 g of the crude diene (51%, 0.357M) are dissolved in 660 ml of tert.butanol in a three-necked sulphonation flask equipped with a stirrer, a reflux condenser, a thermometer and a protecting gas feed pipe with a bubble counter and treated with a solution of 57 g of trimethylamine N-oxide in 232 ml of water. Thereto there are added 150 ml of a 0.05% solution of osmium tetroxide in tert.-butanol. The emulsion is held at reflux temperature for 48 hours with good stirring. The cooled solution is diluted with 300 ml of ether and washed with 300 ml of saturated sodium chloride solution, 325 ml of 2N hydrochloric acid and ice. The organic phase is washed twice with saturated sodium chloride solution. The aqueous phases are extracted twice with ether. After drying the combined organic phases over magnesium sulphate and concentration on a rotary evaporator, there are obtained 130 g of crude product. By recrystallization from hexane there are obtained 85 g (94%) of 2,2,4,5,5,8-hexamethyl-bicyclo[4.4.0]-dec-1(6)-ene-8,9-diol in the form of two isomers.

¹H-NMR: (CDCl₃ 400 MHz): 0.79 (s, 6H); 0.87 (d, J=7 Hz, 3H); 0.872 (d, J=7 Hz, 3H); 0.92 (s, 3H); 0.98 (s, 3H); 0.97 (s, 3H); 0.972 (s, 3H); 1.02 (s, 6H); 1.1 (s, 3H); 1.29 (s, 3H);

MS: 252 M+, 234, 219, 205, 191, 175, 161, 149, 135, 107, 91, 43.

85 g (0.337 mol) of the 2,2,4,5,5,8-hexamethyl-bicyclo[4.4.0]dec-1(6)-ene-8,9-diol are dissolved at room temperature in 218 ml of pyridine. The solution is now cooled to 0° C. and 30.2 ml of methanesulphonyl chloride are slowly added dropwise during 20 minutes. The mixture is stirred at room temperature for a further 24 hours. The mixture is thereupon diluted with ether and washed with 1.480 l of 2N hydrochloric acid and 400 ml of saturated sodium chloride solution. The aqueous phase is extracted with ether and the combined organic phases are washed neutral with dilute sodium bicarbonate solution, dried over sodium sulphate and evaporated.

Spectral data of the mesylate (two isomers):

¹N-NMR: (CDCl₃ 400 MHz): 0.795 (s, 3H); 0.807 (s, 3H); 0.875 (d, J=7 Hz, 3H) 0.877 (d, J=7 Hz, 3H); 1.917 (s, 3H); 1.93 (s, 3H); 1.97 (s, 3H); 1.98 (s, 3H); 1.02 (s, 3H); 1.03 (s, 3H); 1.17 (s, 3H); 1.35 (s, 3H); 3.07 (s, 6H); 4.68 (m, 2H);

MS: 330, 312, 297, 234, 219, 201, 191, 175, 149, 135, 119, 105, 95, 83.

100 g of the crude mesylate are dissolved at room temperature in 575 ml of methanol and this solution is left to react at room temperature for 21 hours with 575 ml of 3N potassium hydroxide solution. The mixture is thereupon diluted with ether and washed with a saturated sodium chloride solution. The aqueous phase is extracted with ether. The combined organic phases are neutralized and dried over magnesium sulphate. 73 g of crude product are obtained. By filtration with hexane over 700 g of silica gel there are firstly obtained 11 g of hexamethyltetralin. Elution with 20% ether/hexane gives 51 g of 2,2,3,5,5-pentamethyl-bicyclo[4,3,0]non-1(6)-en-8-yl methyl ketone (two isomers).

¹H-NMR: (CDCl₃, 400 MHz): 1.78 (s, 3H); 1.79 (s, 3H); 1.86 (d, J=7 Hz, 3H); 1.87 (d, J=7Hz, 3H); 1.95, 1.96, 1.965, 1.98 (4 s, 18H); 2.15 (s, 3H); 2.157 (s, 3H); 2.52 (m, 8H); 3.105 (m, 2H);

MS: 234 M+, 219, 191, 175, 161, 149, 135, 119, 107, 91, 83, 69, 55, 43.

IR: (liquid) 1710 cm⁻¹.

Odour: After ambrette-seeds, musk.

EXAMPLE 4

13 g of hydrocarbon mixture containing 28% of 2,2,4,5,5,8-hexamethyl-bicyclo[4.4.0]deca-1(6),8-diene are dissolved in 80 ml of methanol and 6.5 g (0.01669M) of thallium (III) nitrate are added. After stirring for 30 minutes at room temperature, the thallium (I) nitrate is filtered off and the solution is evaporated in the presence of excess sodium bicarbonate. The crude product is chromatographed over 300 g of silica gel. By elution with 3% ether in hexane there are obtained 900 mg of 2,2,3,5,5-pentamethyl-bicyclo[4.3.0]non-1(6)-en-8-yl methyl ketone and 670 mg of 1-(2,2,4,5,5-pentamethyl-bicyclo[4.3.0]non-1(6)-en-7-yl)-1,1-dimethoxyethane.

Spectral data of the ketal:

¹N-NMR: (CDCl₃, 400 MHz): 0.79 (s, 3H); 0.86 (d, J=7 Hz, 3H); 0.955 (s, 3H); 0.962 (s, 3H); 0.995 (s, 3H); 1.155 (s, 3H); 3.21 (s, 3H); 3.25 (t, J=5 Hz, 1H); 3.38 (s, 3H);

MS: 280 M+, 248, 233, 217, 201, 189, 175, 163, 149, 133, 119, 102, 91, 73, 59.

EXAMPLE 5

300 ml of ethylamine are placed in a three-necked sulphonation flask equipped with a stirrer and a low temperature condenser (filled with CO₂/isopropanol) and then 30 g (0.66M) of ethanol and 48 g (0.22M) of 1,1,4,4,6,7-hexamethyl-1,2,3,4-tetrahydro-naphthalene are added. 4.5 g (0.66M) of lithium are added within 1 hour. The mixture is left to react under reflux. After stirring for 3 hours, the same amounts of lithium and ethanol are added and the mixture is stirred at room temperature overnight. Thereupon, the ethylamine is distilled off and the residue is diluted with hexane. The organic phase is washed neutral with water, dried over sodium sulphate and evaporated. 43.9 g of crude product are obtained. This product contains (according to GC): 7% of starting material, 13% of a substance which is not isolated (probably monoene) and 79% of 2,2,5,5,8,9-hexamethyl-bicyclo[4.4.0]deca-1(6),8-diene.

¹H-NMR: (CDCl₃, 400 MHz): 1 (s, 12H); 1.5 (s, 4H); 1.64 (s, 6H); 2.57 (s, 4H);

MS: 218 M+, 203, 147, 133, 119, 91, 77, 69, 56, 41.

The compound is purified by gas chromatography.

26 g of 2,2,5,5,8,9-hexamethyl-bicyclo[4.4.0]deca-1(6),8-diene and 3 g of sodium acetate in 200 ml of dichloromethane are placed in a sulphonation flask equipped with a stirrer, the mixture is cooled to −20° C. and 19 g of 40% peracetic acid are added dropwise within 5 minutes while stirring. The mixture is stirred at −10° C. for 45 minutes. The mixture is poured into water, washed with saturated sodium pyrosulphite solution and water and evaporated. The crude product (26 g) contains (according to GC) 70% of 8,9-epoxy-2,2,5,5,8,9-hexamethyl-bicyclo-[4.4.0]non-1(6)-ene.

¹H-NMR: (CHCl₃, 400 MHz): 0.94 (s, 6H); 0.98 (s, 6H); 1.34 (s, 6H); 1.44 (m, 4H); 2.21 (d, J=16 Hz, 2H); 2.46 (d, J=16 Hz, 2H);

MS: 234, 219, 201, 191, 177, 161, 135, 119, 107 91, 77, 55, 43.

7.5 g of boron trifluoride etherate are added while stirring to a solution of 26 g of the above crude 8,9-epoxy-2,2,5,5,8,9-hexamethyl-bicyclo[4.4.0]non-1(6)-ene. The temperature rises to 50° C. The mixture is cooled with ice. After stirring for 30 minutes, the mixture is poured into water, washed with saturated sodium bicarbonate solution, dried and evaporated. The crude product (27 g) is chromatographed over 200 g of silica gel. By elution with hexane there are obtained 16 g of 1,1,4,4,6,7-hexamethyl-1,2,3,4-tetrahydro-naphthalene and by elution with 10% ether in hexane there are obtained 6.5 g of 2,2,5,5,8-pentamethyl-bicyclo[4.3.0]non-1(6)-en-8-yl methyl ketone.

¹H-NMR: (CDCl₃, 400 MHz); 0.94 (s, 6H); 0.96 (s, 6H); 1.2 (s, 3H); 1.45 (s, 4H); 2.08 (d, J=13 Hz, 2H); 2.7 (d, J=13 Hz, 2H); 2.13 (s, 3H);

MS: 234 M+, 219, 191, 175, 161, 145, 135, 121, 105, 91, 83, 77, 69, 59, 55.

EXAMPLE 6

A solution of 240 g of 3,6-dichloro-3,6-dimethylheptane in 340 g of toluene is added dropwise within 1 hour to a suspension of 20.8 g of aluminium chloride in 333 g of toluene. The mixture is left to react for 50 minutes, 15 g of aluminium chloride are added thereto and the mixture is left to react for a further 10 minutes. The mixture is poured on to ice and extracted with hexane. The organic phase is washed with water, dried over sodium sulphate and evaporated. 274 g of crude product are obtained.

Spectral data of the mixture of 1,1,4,6-tetramethyl-4-ethyl-1,2,3,4-tetrahydro-naphthalene and 1,4,4,6-tetramethyl-1-ethyl-1,2,3,4-tetrahydro-naphthalene:

$^1$H-NMR: (CDCl$_3$, 400 MHz): 0.76 (t, J=7 Hz, 3H); 0.77 (t, J=7 Hz, 3H); 1.207 (s, 3H); 1.22 (s, 3H); 1.23 (s, 3H); 1.24 (s, 3H); 1.27 (s, 3H); 1.28 (s, 3H); 2.29 (s, 3H); 2.30 (s, 3H); 6.94 (d broad, J=8 Hz, 1H); 7.02 (s broad 1H); 7.105 (s, broad, 1H); 7.11 (d, J=8 Hz, 1H); 7.2 (d, J=8 Hz, 1H);

MS: 216, 201, 187, 173, 145, 131, 115, 105.

700 ml of methylamine are placed in a three necked sulphonation flask equipped with a stirrer and low temperature condenser (filled with CO$_2$/isopropanol) and 237 g of a mixture of 1,1,4,6-tetramethyl-4-ethyl-1,2,3,4-tetrahydronaphthalene and 1,4,4,6-tetramethyl-1-ethyl-1,2,3,4-tetrahydro-naphthalene are added. The mixture is cooled to $-15°$ C. and reacted with two portions of ethanol (93 g and 47 g) and lithium (15.2 g and 7.6 g). The mixture is held at reflux temperature for 12 hours and 47 g of ethanol and 7.6 g of lithium are again added thereto. Thereupon, the methylamine is distilled off. The residue is diluted with hexane and washed with water, dried and evaporated 233 g of crude product are obtained. This product contains according to GC (area percent):

40% of a mixture of 2,5,5,8-tetramethyl-2-ethyl-bicyclo[4.4.0]deca-1(6),8-diene and 2,2,5,8-tetramethyl-5-ethyl-bicyclo[4.4.0]deca-1(6), 8-diene:

$^1$H-NMR: (CDCl$_3$, 400 MHz): 0.737 (3H, t, J=7 Hz); 0.747 (3H, t, J=7 Hz); 0.955 (s, 3H); 0.975 (s, 3H); 0.982 (s, 3H); 0.990 (s, 3H); 1.002 (s, 3H); 1.007 (s, 3H); 1.68 (s, broad, 3H); 1.68 (s. 3H, broad); 5.42 (m, 1H); 5.42 (m, 1H);

MS: 218M$^+$, 203, 189, 175, 173, 159, 147, 133, 199, 105, 91, 77, 69; and

45% of a mixture of cis- and trans-2,5,5,8-tetramethyl-2-ethyl-bicyclo[4.4.0]dec-1(6)-ene and 2,2,5,8-tetramethyl-5-ethyl-bicyclo[4.4.0]-dec-1(6)-ene:

$^1$H-NMR: (CDCl$_3$, 400 MHz): 0.892 (s); 0.905 (s); 0.925 (s); 0.945 (s); 0.950 (s); 0.950 (s); 0.965 (s);

MS: 220M$^+$, 205, 191, 177, 149, 135, 121, 109, 105, 95.

10 g hydrocarbon mixture containing 37% of 2,5,5,8-tetramethyl-2-ethyl-bicyclo[4.4.0]deca-1(6),8-diene and 2,2,5,8-tetramethyl-5-ethyl-bicyclo[4.4.0]deca-1(6),8-diene are dissolved in 200 ml of methanol and 6.62 g of thallium (III) nitrate are added while stirring. After stirring for 1.5 hours, the mixture is filtered and stirred in the presence of an excess of sodium bicarbonate and evaporated. The purification of the product is carried out by chromatography.

Spectral data of the mixture of the cis and trans isomers of 2,5,5-trimethyl-2-ethyl-bicyclo[4.3.0]non-1,6-en-8-yl methyl ketone:

$^1$H-NMR: (CDCl$_3$, 400 MHz): 0.76 (t, J=7 Hz, 3H); 0.76 (t, J=7 Hz, 3H); 0.917 (s, 3H); 0.927 (s, 3H); 0.955 (s, 3H); 0.965 (s, 3H); 0.970 (s, 3H); 0.977 (s, 3H); 2.154 (s, 3H); 2.155 (s, 3H); 3.080 (m, 1H); 3.085 (m, 1H);

IR: (liquid): 1710 cm$^{-1}$;

MS: 234M$^+$, 219, 205, 191, 175, 161, 147, 131, 119, 105, 91, 77, 69, 43.

Odour: Fruity, musk, slightly woody.

EXAMPLE 7

302 g of concentrated sulphuric acid are placed in a three-necked sulphonation flask equipped with a stirrer, cooled at $-10°$ C. and a solution of 99 g of 5-methylhex-1-en-5-ol in 377 g of toluene is slowly added dropwise within 1.25 hours. The mixture is stirred at the same temperature for a further 2.5 hours, then diluted with hexane and poured on to ice. The aqueous phase is extracted twice with hexane. The combined organic phases are washed with a saturated sodium carbonate solution and dried over sodium sulphate. The crude product (126 g) is distilled. In this manner there are obtained 73.8 g of 80% 1,1,4,6-tetramethyl-1,2,3,4-tetrahydro-naphthalene of boiling point 110° C./4×10$^{-2}$ mm Hg.

$^1$H-NMR: (CDCl$_3$, 400 MHz): 1.24 (s, 3H); 1.275 (d, J=7 Hz, 3H); 1.28 (s, 3H); 2.29 (s, 3H); 2.85 (M, 1H); 6.96 (d, J=8 Hz, broad, 1H); 6.98 (s, broad, 1H); 7.21 (d, J=8 Hz, 1H);

MS: 128M$^+$, 173, 137, 143, 131, 115, 105, 91, 77 65, 51, 41.

225 ml of ethylamine are placed in a three-necked sulphonation flask equipped with a stirrer and a low temperature condenser (filled with CO$_2$/isopropanol), then 18.4 g (0.4M) of ethanol and 38 g of 1,1,4,6-tetramethyl-1,2,3,4-tetrahydro-naphthalene (80%) are added. 2.8 g (0.4M) of lithium are added within 10 minutes. The mixture is now stirred at room temperature for 1.5 hours. 10 g of ethanol (0.2M) and 1.5 g of lithium are then added thereto. The mixture is left to react for 2.5 hours. The ethylamine is thereupon distilled off. The residue is diluted with hexane. The organic phase is washed neutral with water, dried over sodium sulphate and evaporated. 35 g of crude product are obtained.

This product contains (according to GC): 43% of 2,2,5,8-tetramethyl-bicyclo[4.4.0]deca-1(6),8-diene.

$^1$H-NMR: (CDCl$_3$, 400 MHz): 0.98 (s, 3H); 0.99 (s, 3H); 1.02 (d, J=7 Hz, 3H); 1.67 (m, 3H); 5.43 (m, 1H);

MS: 190M$^+$, 175, 147, 130, 119, 105, 81, 77, 65, 55, 41.

24 g of crude 2,2,5,8-tetramethyl-bicyclo[4.4.0]deca-1(6),8-diene (43%) in 120 ml of tert.butanol are treated with a solution of 10.5 g of trimethylamine N-oxide in 43 ml of water in a three-necked sulphonation flask equipped with a stirrer, a reflux condenser, a thermometer and an argon flow with a bubble counter. 50 ml of a 0.05% solution of osmium tetroxide in tert.butanol are added thereto. The resulting emulsion is held at reflux temperature for 96 hours with good stirring. The cooled solution is diluted with ether and washed with a saturated sodium chloride solution, with 2N hydrochloric acid and with ice-water. The aqueous phases are extracted twice with ether. After drying the combined organic phases over magnesium sulphate and concentration on a rotary evaporator, 24 g of crude product was obtained. By recrystallization from hexane there are obtained 6 g of 2,2,5,9-tetramethyl-bicyclo[4.4.0]-dec-1(6)-ene-8,9-diol of melting point 121°–123° C.

$^1$H-NMR: (CDCl$_3$, 400 MHz): 0.975 (d, J=7 Hz, 3H); 0.977 (s, 3H); 0.99 (s, 3H); 1.22 (s, 3H); 3.59 (q, J=6 Hz, J=13 Hz, 1H);

MS: 224M$^+$, 206, 191, 177, 163, 150, 135, 121, 107, 95, 74, 55, 43.

5 g (0.0265 mol) of 2,2,5,9-tetramethyl-bicyclo[4.4.0]-dec-1(6)-ene-8,9-diol are dissolved at room temperature in 17 ml of pyridine. The solution is then cooled to 0° C. and 2.36 ml of methanesulphonyl chloride are slowly added dropwise during 20 minutes. The mixture is stirred at room temperature for 24 hours. The mixture is diluted with ether and washed with 1.480 l of 2N hydrochloric acid and 400 ml of saturated sodium chloride solution. The aqueous phase is extracted with ether. The combined organic phases are washed neutral with a dilute sodium bicarbonate solution, dried over sodium sulphate and evaporated. 4.1 g of crude monomesylate are obtained.

$^1$H-NMR: (CDCl$_3$, 400 MHz): 0.97 (d, J=7 Hz, 3H); 0.985 (s, 3H); 1 (s, 3H); 1.29 (s, 3H); 3.07 (s. 3H); 4.68 (q, J=6 Hz, J=7 Hz, 1H);

MS: 287, 267, 206, 173, 163, 147, 131, 121, 107, 95, 91, 79, 69, 57, 41.

4 g of the crude mesylate are dissolved at room temperature in 25.1 ml of methanol and stirred at room temperature for 12 hours with 25.1 ml of 3N potassium hydroxide solution. The mixture is diluted with ether and washed with a saturated sodium chloride solution. The aqueous phase is extracted with ether. The combined organic phases are neutralized and dried over magnesium sulphate. 4 g of crude product are obtained. 1 g of 1,1,4,6-tetramethyltetralin is firstly obtained by filtration with hexane over silica gel. Elution with 20% ether/hexane gives 1.8 g of 2,2,5-trimethyl-bicyclo[4.3.0]non-1(6)-en-8-yl methyl ketone.

$^1$H-NMR: (CDCl$_3$, 400 MHz); 0.965 (s, 3H); 0.9725 (d, J=7 Hz, 3H); 0.98 (s, 6H); 2.16 (s, 3H);

MS: 206M+, 191, 173, 163, 147, 133, 119, 107, 105, 91, 77, 69, 55, 43.

Odour: Damascone-like, ionine-like; after berries, tobacco.

EXAMPLE 8

250 ml of ethylamine are placed in a three-necked sulphonation flask equipped with a stirrer and a low temperature condenser (filled with CO$_2$/isopropanol). 2.36 g of methanol and 8 g of 1,1,6-trimethyl-4-isopropyl-1,2,3,4-tetrahydro-naphthalene are added. 0.5 g (0.074M) of lithium is added within 1 minute. The mixture is left to react under reflux for 12 hours. Thereupon, the same amounts of lithium and methanol are again added and the mixture is stirred at room temperature for 7 hours. The ethylamine is then distilled off and the residue is diluted with hexane. The organic phase is washed neutral with water, dried over sodium sulphate and evaporated. 6.9 g of crude product are obtained. This product contains (according to GC): 88% of 2,2,8-trimethyl-5-isopropyl-bicyclo[4,4,0]nona-1(6),8-diene.

$^1$H-NMR (CDCl$_3$, 400 MHz): 0.71 (d, J=7 Hz, 3H); 0.945 (d, J=7 Hz, 3H); 0.975 (s, 3H); 0.98 (s, 3H); 1.66 (s, broad 3H); 5.43 (m, 1H);

MS: 218M+, 175, 159, 145, 133, 119, 105, 91.

6.9 g of 2,2,8-trimethyl-5-isopropyl-bicyclo[4.4.0]nona-1(6),8-diene are dissolved in 70 g of methanol and 12 g of thallium (III) nitrate are added while stirring. After stirring for 20 minutes at room temperature, the thallium (I) nitrate formed is filtered off and the solution is evaporated in the presence of an excess of sodium bicarbonate. The crude product is chromatographed over 100 g of silica gel. 2 g of 2,2-dimethyl-5-isopropyl-bicyclo[4.3.0]non-1(6)-en-8-yl methyl ketone are obtained.

$^1$H-NMR: (CDCl$_3$, 400 MHz): 0.712 (d, J=7 Hz, 3H); 0.93 (d, J=7H, 3H); 0.965 (s, 6H); 2.165 (s, 3H); 3.115 (m, 1H);

MS: 234M+, 219, 191, 173, 163, 147, 133, 119, 105, 91, 77, 69, 55, 43

IR: (liquid) 1710 cm$^{-1}$

Odour: Fruity, damascone-like.

EXAMPLE 9

7.3 g of 4,5,6,7-tetrahydro-4,4,7,7-tetramethyl-2-indanecarboxylic acid are dissolved in 150 ml of tetrahydrofuran and treated slowly while cooling with ice and stirring vigorously with 47.3 ml of methyl lithium (1.6 molar in ether). After stirring for 3 hours at room temperature, the mixture is poured on to ice, extracted with ether, washed with water, dried over sodium sulphate and evaporated. After distillation of the crude product, there are obtained 5.6 g of 2,2,5,5-tetramethyl-bicyclo[4.3.0]non-1(6)-en-8-yl methyl ketone as a colourless liquid of boiling point 53°–60° C./0.01 mm Hg.

The 4,5,6,7-tetrahydro-4,4,7,7-tetramethyl-2-indanecarboxylic acid used as the starting material can be prepared as follows:

5.3 g of magnesium shavings are covered with 100 ml of ether and 30.8 g of methyl iodide are added dropwise in such a manner that the mixture boils slightly. After the addition of 100 ml of ether, the mixture is held at reflux temperature for a further 3 hours, cooled by means of an ice-bath and treated with 20.7 g of copper (I) iodide. After stirring for 15 minutes at 0° C., a solution of 10 g of 3,6,6-trimethyl-2-cyclohexenone in 40 ml of ether is added and the mixture is stirred at 0° C. for a further 3 hours. The green suspension is subsequently poured on to ice, acidified with 2N hydrochloric acid and extracted with ether. The insoluble constituents of the organic phase are filtered off, the filtrate is washed with dilute sodium thiosulphate solution, dried and evaporated. After distillation of the crude product, there are obtained 8.5 g of 2,2,5,5-tetramethylcyclohexanone as a colourless liquid of boiling point 60°–67° C./13 mm Hg.

106.9 ml of n-butyl lithium (2 molar in hexane) are added dropwise while cooling with ice to a solution of 21.6 g of diisopropylamine in 340 ml of ethylene glycol dimethyl ether. After stirring for 30 minutes at 0° C., a solution of 23.2 g of 2,2,5,5-tetramethylcyclohexanone in 100 ml of ethylene glycol dimethyl ether is added while cooling with ice. The mixture is stirred at room temperature for a further 45 minutes, again cooled to 0° C. and 213.9 g of methyl iodide are added thereto rapidly. The mixture is stirred at 50° C. for 45 minutes, cooled, poured on to ice and extracted with ether. After washing the organic phase with 5% hydrochloric acid and diluted sodium hydrogen carbonate solution, it is dried over sodium sulphate and evaporated. Distillation of the crude product on a spinning band column gives 13.7 g of 2,2,5,5,6-pentamethylcyclohexanone as a colourless liquid of boiling point 86°–94° C./16 mm Hg.

26 g of 2,2,5,5,6-pentamethylcyclohexanone are dissolved in 500 ml of ether and treated slowly at −20° C. with 113.5 ml of methyl lithium (1.5 molar in ether). After stirring for 3.5 hours at 0° C., the mixture is poured on to ice, acidified with 1N hydrochloric acid, extracted with ethyl acetate, dried and evaporated. Distillation of the crude product gives 25.9 g of 1-hydroxy-1,2,2,5,5,6-hexamethylcyclohexane as a colourless liquid of boiling point 87°–92° C./10 mm Hg.

25.9 g of 1-hydroxy-1,2,2,5,5,6-hexamethylcyclohexane are dissolved in 600 ml of benzene and, after the addition of a spatula tip of p-toluenesulphonic acid, held at boiling temperature on a water separator for 3 hours. The mixture is cooled, treated with sodium carbonate, stirred briefly, filtered and the benzene is distilled off at normal pressure. Distillation of the residue gives 21 g of 1,2,3,3,6,6-hexamethyl-1-cyclohexene as a colourless liquid of boiling point 65°–67° C./10 mm Hg.

21 g of 1,2,3,3,6,6-hexamethyl-1-cyclohexene are dissolved in 600 ml of carbon tetrachloride. After the addition of 45 g of N-bromosuccinimide and a spatula tip of α,α'-azoisobutyronitrile, the mixture is held at reflux temperature for 3 hours, cooled, the resulting succinimide is filtered off and the filtrate is evaporated. After filtration of the crude product over silica gel [eluting agent: hexane/ether (2:1)], there are obtained 38 g of 1,2-dibromomethyl-3,3,6,6-tetramethyl-1-cyclohexane as a colourless oil which solidifies in a freezer.

38 g of 1,2-dibromomethyl-3,3,6,6-tetramethyl-1-cyclohexene and 18.7 g of diethyl malonate are dissolved in 150 ml of ethanol and heated to 80° C. At this temperature there is added dropwise a solution of 5.4 g of sodium in 250 ml of ethanol. The mixture is subsequently held at reflux temperature for a further 6 hours. After cooling, the mixture is poured on to ice, acidified with 1N hydrochloric acid, extracted with ether, washed with water and evaporated. This crude product is chromatographed on silica gel [eluting agent: hexane/ether (4:1)]. There are obtained 18.4 g of diethyl 4,5,6,7-tetrahydro-4,4,7,7-tetramethyl-2,2,-indanebiscarboxylate as a not quite uniform colourless oil. The further purification is carried out in the next step.

18.4 g of diethyl 4,5,6,7-tetrahydro-4,4,7,7-tetramethyl-2,2-indanebiscarboxylate are dissolved in 500 ml of ethanol and treated with a solution of 64 g of potassium hydroxide in a mixture of 200 ml of ethanol and 50 ml of water. After heating at reflux temperature for 6 hours, the mixture is cooled, the majority of the alcohol is distilled off on a rotary evaporator, the residue is poured on to ice, acidified with 2N hydrochloric acid, extracted repeatedly with ethyl acetate, dried and evaporated. The thus-obtained crude product is heated to 160° C. for 5.5 hours and subsequently chromatographed on silica gel [eluting agent: hexane/ether (2:1)]. After recrystallization from pentane, there are obtained 6.5 g of 4,5,6,7-tetrahydro-4,4,7,7-tetramethyl-2-indanecarboxylic acid in the form of colourless crystals of melting point 125°–129° C.

In the following formulation Examples,

"compound 1" stands for 2,2,5,5-tetramethyl-bicyclo[4.3.0]non-1(6)-en-8-yl methyl ketone, "compound 2" stands for 2,2,3,5,5-pentamethyl-bicyclo[4.3.0]non-1(6)-en-8-yl methyl ketone, "compound 3" stands for 2,2,5-trimethyl-bicyclo[4.3.0]non-1(6)-en-8-yl methyl ketone, "compound 4" stands for 2,5,5-trimethyl-2-ethyl-bicyclo[4.3.0]non-1(6)-en-8-yl methyl ketone and "compound 5" stands for 2,2,5,5,8-pentamethyl-bicyclo[4.3.0]non-1(6)-en-8-yl methyl ketone.

EXAMPLE 10

| A. Raspberry flavour | | |
|---|---|---|
| | Parts by weight | |
| Ethyl palmitate | 0.05 | 0.05 |
| Geraniol | 0.2 | 0.2 |
| Methylionone | 0.6 | 0.6 |
| Ethyl vanillin | 1.0 | 1.0 |
| Amyl valerate | 1.0 | 1.0 |
| Benzyl acetate | 2.0 | 2.0 |
| $C_{16}$-aldehyde | 2.5 | 2.5 |
| Ethyl formate | 4.0 | 4.0 |
| Amyl acetate | 6.0 | 6.0 |
| Ethyl butyrate | 6.0 | 6.0 |
| Isobutyl acetate | 23.0 | 23.0 |

| -continued | | |
|---|---|---|
| A. Raspberry flavour | | |
| | Parts by weight | |
| Ethyl acetate | 33.5 | 33.5 |
| Propylene glycol | 920.15 | 905.15 |
| Compound 1 (10% in ethanol) | — | 15.0 |
| | 1,000.00 | 1,000.00 |

By adding compound 1 to the above composition the methylionone note present is altered very advantageously from the point of view of odour and flavour; there appears a fruity note which is reminiscent of fully ripe raspberries.

| B. Tobacco flavour | | |
|---|---|---|
| | Parts by weight | |
| Linalyl acetate (10% in ethanol) | 0.3 | 0.3 |
| Cinnamaldehyde (10% alcoholic) | 0.4 | 0.4 |
| Geraniol | 0.5 | 0.5 |
| Angelica root oil | 0.5 | 0.5 |
| Amyl butyrate | 1.0 | 1.0 |
| Amyl valerate | 1.0 | 1.0 |
| Vanillin | 2.0 | 2.0 |
| $C_{18}$-aldehyde | 2.0 | 2.0 |
| Petitgrain oil (Paraguay) | 2.0 | 2.0 |
| Benzaldehyde | 2.5 | 2.5 |
| Orange oil (concentrated 10-fold) | 5.0 | 5.0 |
| $C_{14}$-aldehyde | 15.0 | 15.0 |
| Alcohol | 967.8 | 957.8 |
| Compound 1 | — | 10.0 |
| | 1,000.0 | 1,000.0 |

By adding compound 1 to the above composition the fruity note present in the composition is clearly intensified. The slightly fatty note is advantageously enveloped (covered); there appears an additional note which is reminiscent of fully ripe apricots.

In the incorporation of the composition in tobacco the intensified fruity note is of advantage and in addition, the tobacco note present is intensified in an advantageous manner.

| uz,8/25 C. General flowery perfumery base | |
|---|---|
| | Parts by weight |
| Terpineol | 260 |
| Hydroxycitronellal | 220 |
| Cinnamic alcohol substitute | 120 |
| Phenylethyl alcohol | 100 |
| Cinnamyl formate | 20 |
| Linalool | 15 |
| Terpenyl acetate | 10 |
| Musk ketone | 10 |
| Geranyl acetate | 10 |
| Jasmine (synthetic) | 10 |
| Eugenol | 5 |
| Indole [10% in dipropylene glycol (DPG)] | 5 |
| $C_{10}$-aldehyde (10% in DPG) | 5 |
| p-Methylacetophenone | 5 |
| Undecalactone | 5 |
| | 500 |

By adding 200 parts of compound 1 the composition becomes much softer and receives a note in the direction of strawberry; it is now especially suitable for the perfuming of cosmetics.

| D. Perfumery complex in the direction of eau de cologne | |
|---|---|
| | Parts by weight |
| Bergamot oil | 200 |

| D. Perfumery complex in the direction of eau de cologne | |
| --- | --- |
| | Parts by weight |
| Methyl dihydrojasmonate | 200 |
| Sandalwood oil | 200 |

If 50 parts of compound 1 are added to this complex, then the dominating sandal character of the bottom note is advantageously enveloped by a very warm and very powerful musk note which confers substantially more volume to the complex. When freshly dipped, the characteristic citrus effect now combines very impressively with the musk note of the novel compound. This simple complex is excellently suited for men's colognes.

| E. Perfumery composition with a rose character | |
| --- | --- |
| | Parts by weight |
| Phenylethyl alcohol | 300 |
| Geraniol | 250 |
| Jasmine "lavage" (aqueous distillate) | 200 |
| Citronellol (extra) | 100 |
| Musk ketone | 50 |
| α-Ionone | 30 |
| $C_{10}$-aldehyde (10% in propylene glycol) | 5 |
| $C_{11}$-aldehyde (10% in propylene glycol) | 5 |
| | 940 |

By adding 60 parts of compound 1 the rose base becomes much rounder, softer and, moreover, receives a fresher character.

| F. Perfumery chypre | |
| --- | --- |
| | Parts by weight |
| 1-Methylcyclododecyl methyl ether | 200 |
| Bergamot oil | 150 |
| Hydroxycitronellal | 100 |
| Pine oil (Pumillon) | 80 |
| Citronellol | 80 |
| Petitgrain oil | 60 |
| Musk 174 TM Givaudan (12-oxahexadecanolide) | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss (decolorized) | 20 |
| | 960 |

By adding 40 parts of compound 1 this cyphre composition becomes much more powerful, not only freshly dipped but also in the bottom(note). Here the novel compound clearly shows the effect which combines the components.

| G. Perfumery base with a fruity character | |
| --- | --- |
| | Parts by weight |
| Ethyl-methyl-phenyl glycidate | 50 |
| Ethyl acetoacetate | 15 |
| Dimethyl-benzyl butyrate | 15 |
| Maltyl isobutyrate | 10 |
| Benzyl acetate | 10 |
| Ethyl acetate | 5 |
| Lemon oil | 5 |
| Dipropylene glycol | 890 |
| | 970 |

If 30 parts of compound 1 are added to this generally fruity base, then it is transformed very pleasantly in the direction of exotic fruit. It now becomes much softer and fresher. Surprisingly, the compound also brings about an enrichment of the top notes.

| H. Perfumery base with a generally flowery character | |
| --- | --- |
| | Parts by weight |
| Terpineol | 260 |
| Hydroxycitronellal | 220 |
| Cinnamic alcohol (substitute) | 100 |
| Cinnamyl formate | 20 |
| Linalool | 15 |
| Terpenyl acetate | 10 |
| Musk ketone | 10 |
| Geranyl acetate | 10 |
| Jasmine (synthetic) | 10 |
| Eugenol | 5 |
| Indole (10% in DPG) | 5 |
| $C_{10}$-aldehyde (10% in DPG) | 5 |
| p-Methylacetophenone | 5 |
| Undecalactone | 5 |
| DPG | 100 |
| | 900 |

An addition of 100 parts of compound 2 produces a very pleasant musk character which makes this previously merely generally flowery base usable for perfumery. On the other hand, with 100 parts of compound 3 a fine violet effect is obtained.

| J. Perfumery base with a fruity character | |
| --- | --- |
| | Parts by weight |
| Ethyl-methyl-phenyl-glycidate | 50 |
| Ethyl acetoacetate | 15 |
| Dimethyl-benzyl butyrate | 15 |
| Maltyl isobutyrate | 10 |
| Benzyl acetate | 10 |
| Ethyl acetate | 5 |
| Lemon oil | 5 |
| Dipropylene glycol | 795 |
| | 900 |

With 100 parts of compound 4 there is obtained from the generally fruity composition a very sweet apple composition. On the other hand, the addition of 100 parts of compound 2 produces a thibetolide effect (musk effect) which conveys the impression of a blackberry.

| K. Perfumery base in the direction of chypre | |
| --- | --- |
| | Parts by weight |
| 1-Methyl-cyclododecyl methyl ether | 200 |
| Bergamot oil | 150 |
| Hydroxycitronellal | 100 |
| Pine needle oil | 80 |
| Citronellol | 80 |
| Petitgrain oil | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss (decolorized) | 20 |
| Dipropylene glycol | 60 |
| | 960 |

By means of 40 parts of compound 4 there is obtained in the originally unspecific chypre base an interesting fruity effect. 40 parts of compound 3 convey a fine violet effect.

| L. Perfumery base in the direction of rose | |
| --- | --- |
| | Parts by weight |
| Phenylethyl alcohol | 300 |
| Geraniol | 250 |
| Jasmine "lavage" (aqueous distillate) | 200 |
| Citronellol (extra) | 100 |
| α-Ionone | 40 |
| $C_{10}$-aldehyde (10% in dipropylene glycol) | 5 |
| $C_{11}$-aldehyde (10% in dipropylene glycol) | 5 |
| | 900 |

The addition of 100 parts of compound 2 produces a character which formerly could only be obtained with the much more expensive thibetolide. The addition of 100 parts of compound 3 produces a very fine violet effect.

| M. Perfumery base in the direction of tobacco | |
| --- | --- |
| | Parts by weight |
| α-Tert.butylcyclohexyl acetate | 400 |
| Jasmine oil (synthetic) | 300 |
| Musk ketone | 40 |
| Sandela ® [3-isocamphyl-(5)-cyclohexanol] | 40 |
| Styrallyl acetate | 30 |
| Coumarin | 20 |
| Isobutylquinoline (10% in DPG) | 10 |
| Lavender oil | 10 |
| Vetiver oil | 10 |
| Galbanum oil | 10 |
| Vassura oil | 10 |
| Dipropylene glycol | 40 |
| | 920 |

By adding 80 parts of compound 5 a fine herby side effect is produced in the tobacco base. With 80 parts of compound 3 a violet note is obtained in this base. An addition of 80 parts of compound 2 produces a musk note.

| Perfumery base in the direction of tulip | |
| --- | --- |
| | Parts by weight |
| Phenylethyl alcohol | 100 |
| Myraldylacetat ™ [4-(4-methyl-3-pentenyl)-3-cyclohexen-1-yl]methyl acetate | 100 |
| Methyl dihydrojasmonate | 100 |
| Acetal CD (glycerine acetal of phenylacetaldehyde) | 100 |
| Hydroxycitronellal | 160 |
| Farnesol | 40 |
| Hexyl salicylate | 30 |
| Terpineol | 30 |
| Cyclamen aldehyde | 20 |
| Linalool | 20 |
| Linalyl anthranilate | 10 |
| Amyl salicylate | 10 |
| $C_{11}$-aldehyde (10% in DPG) | 10 |
| Benzyl acetate | 8 |
| Hexenyl benzoate | 8 |
| Hexenyl acetate (10% in DPG) | 8 |
| p-Cresyl isobutyrate (10% in DPG) | 6 |
| Indole (10% in DPG) | 6 |
| Syringa aldehyde | 4 |
| Dimethyl acetal hydratropaldehyde (10% in DPG) | 30 |
| DPG | 100 |
| | 900 |

From this fantasy composition (tulip) there can be obtained with an addition of 100 parts of compound 4 a very fine fruity dog rose note which represents a clear improvement. With the addition of the same amount of compound 2 a fine musk note in the direction of thibetolide is produced not only in the bottom note but also in the top note. By adding 100 parts of compound 3 a violet note is obtained from the tulip. Moreover, a warm-fruity character can be established in the bottom.

| O. Perfumery base in the direction of leather | |
| --- | --- |
| | Parts by weight |
| Styrax (natural) | 250 |
| Castoreum (anhydrous) | 150 |
| Bergamot oil | 100 |
| Musk infusion (3% in ethanol) | 100 |
| Vetiver oil | 100 |
| Labdanum resinoid | 100 |
| Birch tar (dephenolized, 10% in DPG) | 50 |
| Musk ketone | 25 |
| Sandalwood oil | 10 |
| Vanillin | 10 |
| Ciste labdanum (Spanish) | 5 |
| Dipropylene glycol | 60 |
| | 960 |

By adding 40 parts of compound 3 a violet effect is obtained in the above leather base.

We claim:

1. A fragrance composition comprising an olfactorily effective amount of a compound of the formula

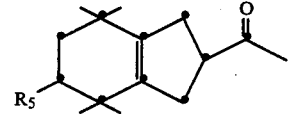   I wherein:
 $R_5$ represents hydrogen and methyl.

2. A fragrance composition according to claim 1 wherein the compound is 2,2,5,5-tetramethylbicyclo[4.3.0]non-1(6)-en-8-yl methyl ketone.

3. A fragrance composition according to claim 1 wherein the compound 2,2,3,5,5-pentamethylbicyclo[4.3.0]non-1(6)-en-8-yl methyl ketone.

4. A flavor composition containing an effective amount of a compound of the formula

   I wherein
 $R_5$ represents hydrogen or methyl, and at least one other flavor agent.

5. A flavor composition according to claim 4 wherein the compound is 2,2,5,5-tetramethylbicyclo[4.3.0]non-1(6)-en-8-yl methyl ketone.

6. A flavor composition according to claim 4 wherein the compound is 2,2,3,5,5-pentamethylbicyclo[4.3.0]-non-1(6)-en-8-yl methyl ketone.

7. A compound of the formula

wherein
R₅ represents hydrogen or methyl.
8. A compound according to claim 7 which is 2,2,5,5-tetramethylbicyclo[4.3.0]non-1(6)-en-8-yl methyl ketone.
9. A compound according to claim 7 which is 2,2,3,5,5-pentamethylbicyclo[4.3.0]non-1(6)-en-8-yl methyl ketone.
* * * * *